United States Patent
Ron (10) Patent No.: US 12,390,218 B2
(45) Date of Patent: Aug. 19, 2025

(54) CLIP FOR EYE MUSCLE SURGERY (71) Applicant: Rambam MedTech Ltd., Haifa (IL)

(72) Inventor: Yonina Ron, Habonim (IL)

(73) Assignee: RAMBAM MEDTECH LTD., Haifa (IL)

(*) Notice: Subject to any disclaimer, the term of this patent is extended or adjusted under 35 U.S.C. 154(b) by 227 days.

(21) Appl. No.: 18/035,203

(22) PCT Filed: Nov. 9, 2021

(86) PCT No.: PCT/IL2021/051323
§ 371 (c)(1),
(2) Date: May 3, 2023

(87) PCT Pub. No.: WO2022/101899
PCT Pub. Date: May 19, 2022

(65) Prior Publication Data
US 2023/0414216 A1 Dec. 28, 2023

Related U.S. Application Data (60) Provisional application No. 63/112,675, filed on Nov. 12, 2020.

(51) Int. Cl.
A61F 9/007 (2006.01)
A61B 17/064 (2006.01)
(Continued)

(52) U.S. Cl.
CPC ...... *A61B 17/0643* (2013.01); *A61B 17/0644* (2013.01); *A61B 17/083* (2013.01);
(Continued)

(58) Field of Classification Search
CPC . A61B 17/083; A61B 17/068; A61B 17/0682; A61B 17/122; A61B 17/128;
(Continued)

(56) References Cited

U.S. PATENT DOCUMENTS

| 4,519,392 A | 5/1985 | Lingua |
| 5,342,389 A | 8/1994 | Haber et al. |

(Continued)

FOREIGN PATENT DOCUMENTS

| EP | 0780107 | 6/1997 |
| WO | 2022/101899 | 5/2022 |

OTHER PUBLICATIONS

U.S. Appl. No. 63/112,675, filed Nov. 12, 2020.
(Continued)

*Primary Examiner* — Majid Jamialahmadi
(74) *Attorney, Agent, or Firm* — Sughrue Mion, PLLC (57) ABSTRACT

An extraocular muscle clip (22) for correcting strabismus includes upper and lower plates (24, 26) which are couplable together to sandwich and grasp extraocular muscle (42). A delivery tool (50) delivers the clip (22) and includes a shaft (52) and a muscle hook (56) that is slidable underneath the extraocular muscle (42) to position the lower plate (26) of the clip (22) underneath the muscle (42). An integrated blade (60) of the tool (50) cuts the extraocular muscle (42) subsequently to grasping of the muscle (42) by the upper and lower plates (24, 26) of the clip (22). One or more sutures (30) are coupled to the upper plate (24) and/or the lower plate (26) of the clip (22) and facilitate recoupling of the extraocular muscle (42) to a globe of the eye (40) following cutting of the extraocular muscle (42). Other embodiments are also described.

7 Claims, 7 Drawing Sheets (51) Int. Cl.
  *A61B 17/08* (2006.01)
  *A61B 17/10* (2006.01)
  A61B 17/00 (2006.01)
  A61B 17/06 (2006.01)
  A61B 17/3211 (2006.01)
  A61F 2/08 (2006.01)

(52) U.S. Cl.
  CPC .............. *A61B 17/10* (2013.01); *A61F 9/007* (2013.01); *A61B 2017/00004* (2013.01); *A61B 17/06* (2013.01); *A61B 2017/0641* (2013.01); *A61B 2017/32113* (2013.01); *A61F 2002/0894* (2013.01)

(58) Field of Classification Search
  CPC . A61B 17/10; A61B 17/0684; A61B 17/0686; A61F 9/007
  See application file for complete search history.

(56) References Cited

U.S. PATENT DOCUMENTS

| | | | |
|---|---|---|---|
| 5,722,982 | A | 3/1998 | Ferreira et al. |
| 5,797,932 | A | 8/1998 | Min et al. |
| 5,925,052 | A * | 7/1999 | Simmons ............. A61B 17/128 606/139 |
| 6,080,169 | A | 6/2000 | Turtel |
| 6,733,510 | B1 | 5/2004 | Melvin |
| 7,399,304 | B2 | 7/2008 | Gambale et al. |
| 10,206,673 | B2 | 2/2019 | Maisano et al. |
| 10,231,825 | B2 | 3/2019 | Alhourani |
| 2005/0049702 | A1 | 3/2005 | Melvin |
| 2005/0125015 | A1 | 6/2005 | Mcnally-Heintzelman et al. |
| 2007/0032800 | A1 | 2/2007 | Ortiz et al. |
| 2015/0359538 | A1* | 12/2015 | Yeatts, II ............. A61B 17/122 606/120 |
| 2017/0319382 | A1 | 11/2017 | Moon et al. |

OTHER PUBLICATIONS

An International Preliminary Report on Patentability dated May 16, 2023, which issued during the prosecution of Applicants PCT/IL2021/051323.

An International Search Report and a Written Opinion both dated Jan. 31, 2022, which issued during the prosecution of Applicants PCT/IL2021/051323.

European Search Report dated Jul. 19, 2024 which issued during the prosecution of European App No. 21891356.4.

Helveston, E. "Surgical Management of Strabismus." Wayenborgh (2005).

McKeown, C. A. (Jun. 4, 2016). Strabismus surgery. Ento Key. https://entokey.com/strabismus-surgery-2/#bb0010.

* cited by examiner

FIG. 9

CLIP FOR EYE MUSCLE SURGERY

CROSS-REFERENCES TO RELATED APPLICATION

The present application is the US National Phase of PCT application PCT/IL2021/051323 to Ron, filed Nov. 9, 2021, entitled "Clip for eye muscle surgery," which published as WO 2022/101899, and which claims priority from U.S. Provisional Patent Application 63/112,675 to Ron, filed Nov. 12, 2020, entitled "Clip for eye muscle surgery," and which is incorporated herein by reference.

FIELD OF THE INVENTION

The present application relates to a device and procedures performed on an eye of a patient. In particular, the present application relates to methods and devices for extraocular muscle manipulations and correcting strabismus.

BACKGROUND

Strabismus is a condition in which the eyes do not properly align with each other when looking at an object. Strabismus can occur due to extraocular muscle dysfunction, neurological problems, trauma or infections. Types of strabismus include esotropia, where the eyes converge (cross-eyed), exotropia, where the eyes diverge and hypertropia where they are vertically misaligned.

Treatment to straighten the eyes is needed. Strabismus surgery (or extraocular muscle surgery, eye muscle surgery, or eye alignment surgery) is surgery on the extraocular muscles to correct strabismus.

SUMMARY OF THE APPLICATION

This summary is meant to provide some examples and is not intended to be limiting of the scope of the invention in any way. For example, any feature included in an example of this summary is not required by the claims, unless the claims explicitly recite the features. Also, the features, components, steps, concepts, etc. described in examples in this summary and elsewhere in this disclosure can be combined in a variety of ways. Various features and steps as described elsewhere in this disclosure may be included in the examples summarized here.

In some applications of the present invention, devices and methods are described herein for performing strabismus surgery on an eye to correct strabismus of the eye, using an extraocular muscle clip and an elongate delivery tool that comprises (a) a muscle hook that is reversibly coupled to the extraocular muscle clip, and (b) an integrated blade moveable so as to cut the extraocular muscle subsequently to grasping of the extraocular muscle by the extraocular muscle clip.

The extraocular muscle clip typically comprises an upper plate and a lower plate, which are distanced from each other when in a delivery state, and are couplable together to sandwich and grasp an extraocular muscle when in a grasping state. For some applications, the muscle clip comprises a hinge coupling the upper plate and lower plate. Typically, but not necessarily, the muscle clip is dissolvable.

The elongate delivery tool is used to deliver the extraocular muscle clip to the extraocular muscle. The upper plate of the muscle clip is disposed adjacent to a delivery shaft of the delivery tool. For some applications of the present invention, the delivery tool shaft comprises a tube, and the upper plate is disposed within a lumen of the shaft of the delivery tool. The delivery tool comprises a muscle hook which extends at a nonzero angle with respect to the shaft of the delivery tool. The muscle hook is reversibly coupled to the extraocular muscle clip. For some applications, the muscle hook comprises a mount which comprises a coupling that reversibly couples to the delivery tool a portion of the extraocular muscle clip, e.g., the lower plate of the muscle clip. The muscle hook of the delivery tool is slid and placed under the extraocular muscle in order to position the lower plate of the muscle clip under the muscle.

Once the lower plate is positioned underneath the muscle, the upper plate of the muscle clip is coupled together with the lower plate in order to sandwich the muscle between the upper and lower plates and grasp the extraocular muscle. For some applications of the present invention, the delivery tool delivers the upper plate above the extraocular muscle such that the upper plate is movable toward an upper surface of the extraocular muscle and is couplable together with the lower plate. For some applications, the delivery tool comprises an arm reversibly coupled to the upper plate. The arm is configured to facilitate movement of the upper plate and coupling together the upper plate and the lower plate into the grasping state. For some applications of the present invention, the delivery tool does not comprise the arm, and the operating physician pushes closed the upper plate toward the lower plate.

The integrated blade of the delivery tool is moveable with respect to the elongate shaft so as to cut the extraocular muscle subsequently to grasping of the extraocular muscle by the upper and lower plates of the extraocular muscle clip. For some applications of the present invention, during delivery of the muscle clip toward the extraocular muscle and during grasping of the muscle by the clip, the integrated blade is kept in an unengaged position in which the blade is generally in alignment with the shaft of the delivery tool. For some applications of the present invention, the shaft of the delivery tool comprises a tube, and the blade is disposed in part within the lumen of the tube. Once the muscle is grasped by the clip, the integrated blade is moved away from the longitudinal axis of the shaft of the delivery tool and toward the muscle hook in order to sever the extraocular muscle. Typically, the muscle hook functions as a safety mechanism by preventing the integrated blade form moving beyond the muscle hook, thereby preventing inadvertent cutting of the sclera by the blade.

Unlike conventional techniques which typically utilize a separate tool for cutting the extraocular muscle, the delivery tool of an application of the present invention provides a single tool which combines the functions of (1) delivering a muscle clip to the extraocular muscle, (2) facilitating grasping the extraocular muscle with the muscle clip, as well as subsequently (3) disinserting the extraocular muscle by cutting the muscle with the blade that is integrated with the delivery tool. In addition, since the delivery tool of an application of the present invention comprises an integrated blade as well as the muscle hook, the muscle hook of the delivery tool provides a safety which prevents the blade from moving beyond the muscle hook, unlike conventional techniques which use a separate cutting instrument (scissors or a scalpel) to cut the tissue without providing a buffer between the scalpel and the sclera.

Additionally, the delivery tool (in particular, the muscle hook and the integrated blade) and the clip of an application of the present invention provide a system for more rapid and more precise (1) gasping of the extraocular muscle by the clip and (2) cutting of the extraocular muscle by the integrated blade.

The muscle clip typically comprises one or more sutures coupled to at least one of the upper plate or the lower plate of the muscle clip. For some applications, the one or more sutures are threaded through at least one of the upper plate or the lower plate of the muscle clip. The one or more sutures are configured to facilitate recoupling of the extraocular muscle to the globe of the eye of following cutting of the extraocular muscle by the integrated blade. Unlike conventional techniques which cut the muscle with a blade and then suture the muscle to the globe of the eye, the system of an application of the present invention provides a muscle clip with an integrated suture that is used to recouple the extraocular muscle to the globe of the eye following the cutting. It is hypothesized by the inventor that this is particularly advantageous, because the extraocular muscle is first grasped by the clip and secured by the clip before it is disinserted. Only once the muscle is secured by the muscle clip is it disinserted and then can easily by imbricated due to the presence of the suture that is coupled to the muscle clip.

The clip of an application of the present invention eliminates the need to suture the suture through the extraocular muscle that has been disinserted from the globe. This is advantageous in (1) the hang-back procedure in which the disinserted muscle is sutured directly to the stump from the original insertion or to the sclera in a vicinity of stump (e.g., underneath the stump) from the original insertion, as well as in (2) procedures in which the extraocular muscle is sutured directly to the sclera (e.g., not in a hang-back procedure) and not back through the poles of the stump of the original insertion, or (3) any other ocular surgical procedure that involves manipulation of the extraocular muscle. The clip of an application of the present invention eliminates the need to imbricate the suture through the disinserted extraocular muscle which, whereby each entry and exit of the suture through the disinserted extraocular muscle increases the likelihood of perforating the eye globe and/or causes additional strain on the sclera during the imbricating of the suture through the disinserted extraocular muscle. The clip of an application of the present invention eliminates the need for imbricating the suture through the disinserted extraocular muscle because the clip couples the suture to the disinserted extraocular muscle via the coupling together of the plates of the clip. Additionally, the extraocular muscle clip of an application of the present invention eliminates the need for a removable clamp which is sometimes used during resection procedures.

The clip and the delivery tool of an application of the present invention may be used for any type of strabismus surgery, e.g., recession and/or resection.

There is therefore provided, in accordance with some applications of the present invention, apparatus for use in correcting strabismus of an eye of a patient, the apparatus including:

an extraocular muscle clip including an upper plate and a lower plate, which are distanced from each other when in a delivery state of the extraocular muscle clip, and are couplable together to sandwich and grasp an extraocular muscle when in a grasping state of the extraocular muscle clip;

an elongate delivery tool configured to deliver the muscle clip when in the delivery state, the elongate delivery tool including:

an elongate shaft; and a muscle hook at a distal end of the elongate shaft being slidable underneath the extraocular muscle, the muscle clip being reversibly coupled to the elongate shaft, the lower plate of the muscle clip being reversibly coupled to the muscle hook so as to be slidable underneath the extraocular muscle, the delivery tool being configured to deliver the upper plate above the extraocular muscle such that the upper plate is movable toward an upper surface of the extraocular muscle and couplable together with the lower plate to sandwich and grasp the extraocular muscle; and an integrated blade moveable with respect to the elongate shaft so as to cut the extraocular muscle subsequently to grasping of the extraocular muscle by the upper and lower plates of the extraocular muscle clip; and one or more sutures coupled to at least one of the upper plate or the lower plate of the muscle clip, the one or more sutures being configured to facilitate recoupling of the extraocular muscle to a globe of the eye of following cutting of the extraocular muscle by the integrated blade.

In some applications of the present invention, the elongate shaft includes a tube, and the integrated blade is slidable at least in part within a lumen of the tube of the delivery tool and exposable from within the lumen of the tube so as to cut the extraocular muscle.

In some applications of the present invention, the muscle clip includes a hinge coupling the upper plate and lower plate.

In some applications of the present invention, the muscle hook is coupled to the elongate shaft, and the muscle hook prevents movement of the blade beyond the muscle hook.

In some applications of the present invention, the extraocular muscle clip is dissolvable.

In some applications of the present invention, the delivery tool includes an arm reversibly coupled to the upper plate, the arm being configured to facilitate movement of the upper plate and coupling together the upper plate and the lower plate into the grasping state.

In some applications of the present invention, the one or more sutures is threaded through at least one of the upper plate or the lower plate of the muscle clip.

There is also provided, in accordance with some applications of the present invention, a method for correcting strabismus of an eye of a patient, the method including:

delivering an extraocular muscle clip including an upper plate and a lower plate to an extraocular muscle using an elongate delivery tool including:

an elongate shaft reversibly coupled to the extraocular muscle clip, a muscle hook at a distal end of the elongate shaft, the muscle clip being reversibly coupled to the elongate tube in a manner in which the lower plate of the muscle clip is coupled to the muscle hook and is distanced from the upper plate during the delivering;

positioning the lower plate underneath the extraocular muscle by sliding the muscle hook underneath the extraocular muscle;

subsequently to the positioning:

moving the upper plate of the muscle clip to an upper surface of the extraocular muscle;

sandwiching the extraocular muscle between the upper and lower plates; and grasping the extraocular muscle between the upper and lower plates by coupling together the upper and lower plates;

subsequently to the grasping:
  distally moving an integrated blade of the delivery tool with respect to the elongate shaft of the elongate delivery tool; and
  cutting the extraocular muscle with the integrated blade; and subsequently to the cutting, recoupling the extraocular muscle to the eye by suturing to the eye one or more sutures coupled to at least one of the upper plate or the lower plate of the muscle clip and by the suturing, drawing the muscle clip and the extraocular muscle grasped by the muscle clip toward the eye.

The present invention will be more fully understood from the following detailed description of embodiments thereof, taken together with the drawings, in which:

DETAILED DESCRIPTION OF APPLICATIONS

Figure 1:
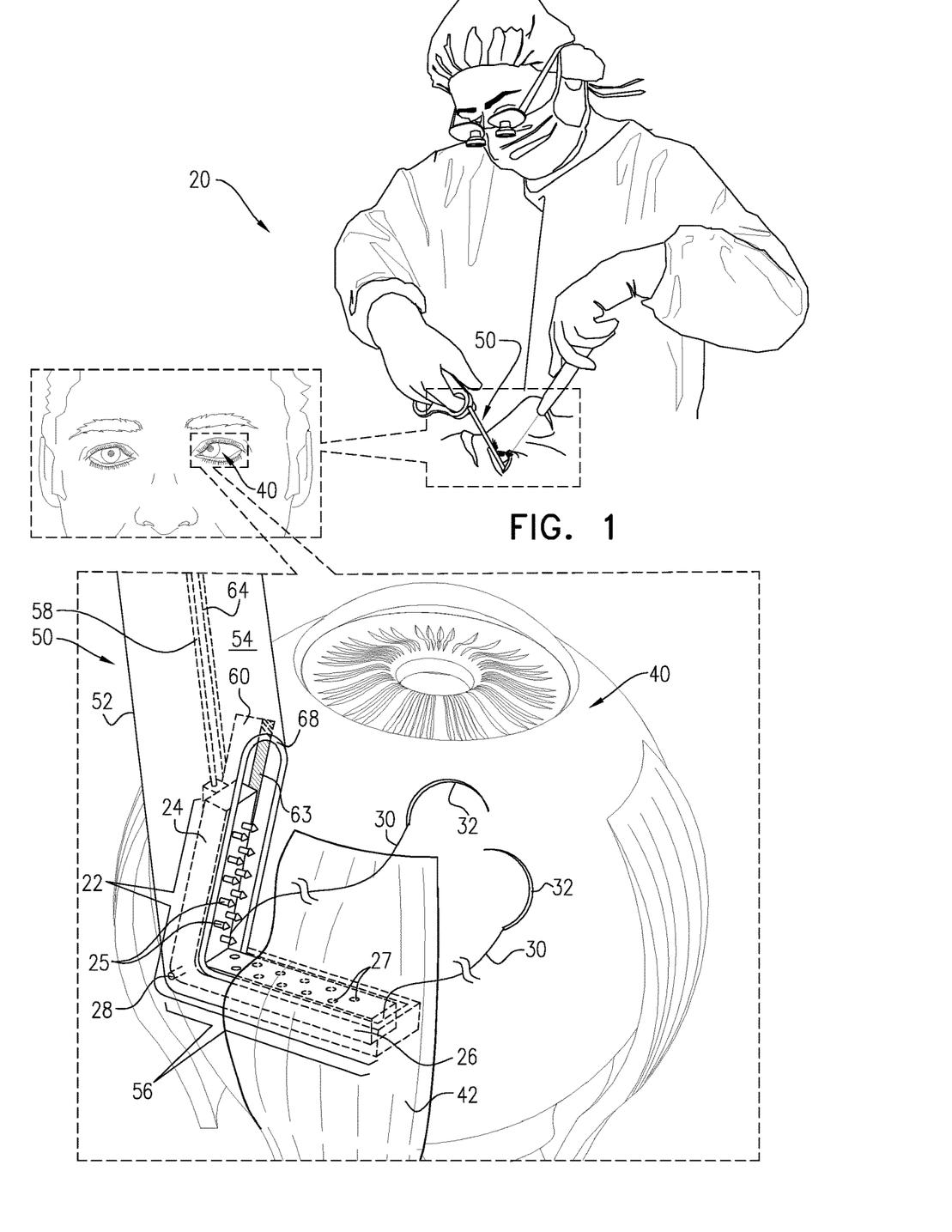
FIG. 1 is a schematic illustration of a delivery tool coupled to an extraocular muscle clip being delivered to an extraocular muscle of an eye of a patient, in accordance with some applications of the present invention.
Figure 6:
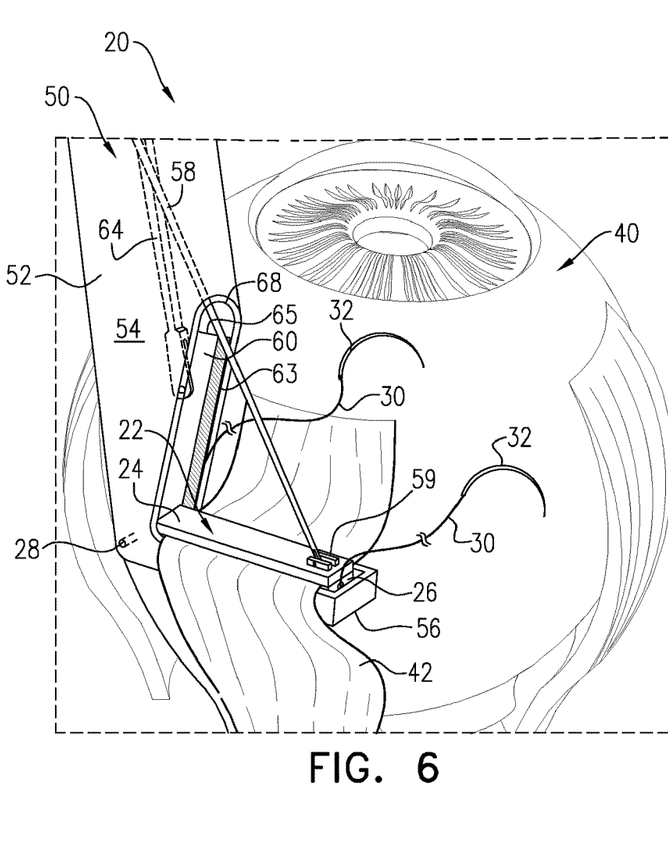
Figure 7:
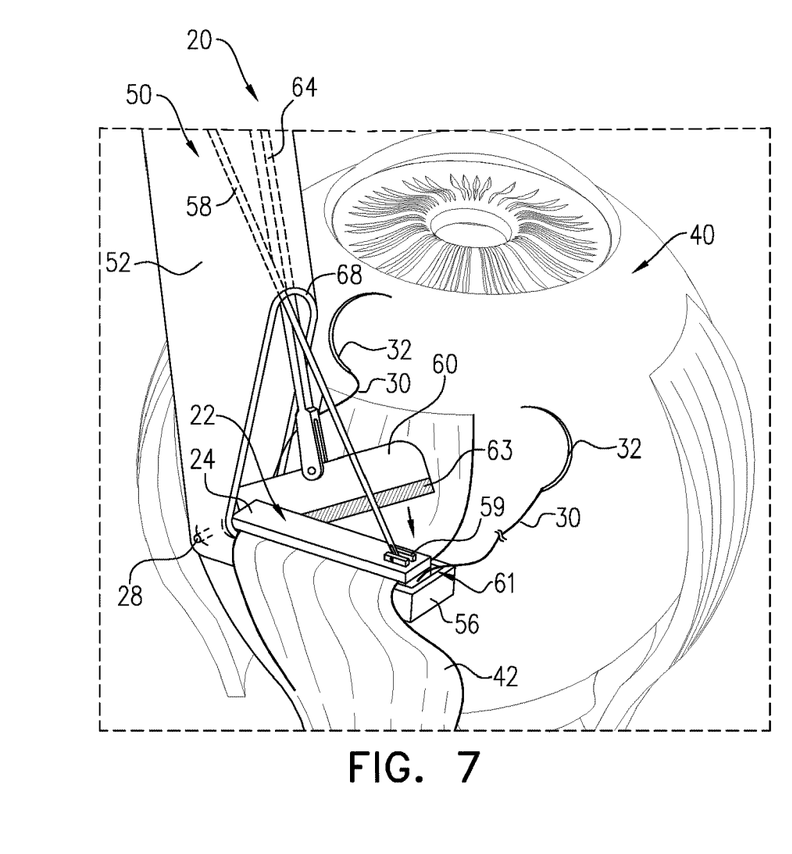

Reference is now made to FIG. 1, which is a schematic illustration of a system 20 comprising an extraocular muscle clip 22 reversibly coupled to a muscle hook 56 of an elongate delivery tool 50, in accordance with some applications of the present invention. Delivery tool 50 comprises an elongate shaft 52 and muscle hook 56 disposed at a distal end of shaft 52 typically at a non-zero angle with respect to shaft 52. For some applications, hook 56 is fixedly coupled to shaft 52. Muscle clip 22 is reversibly coupled to elongate shaft 52. Muscle clip 22 typically comprises an upper coupling element, e.g., an upper plate 24, and a lower coupling element, e.g., a lower plate 26, which are moveable toward each other, typically by moving upper plate 24 toward lower plate 26. Upper and lower plates 24 and 26 are distanced from each other when in a delivery state (as shown in FIG. 1), and are couplable together (as shown in FIG. 6) to sandwich and grasp an extraocular muscle 42 when in a grasping state. Delivery tool 50 comprises an integrated blade 60 moveable with respect to elongate shaft 52 so as to cut extraocular muscle 42 subsequently to grasping of extraocular muscle 42 by upper and lower plates 24 and 26 of extraocular muscle clip 22, such as shown in FIG. 7.

(It is to be noted that in the context of the specification and the claims, the verb "clip" means grab, clamp, or grasp and does not mean cut.)

Figure 3A:
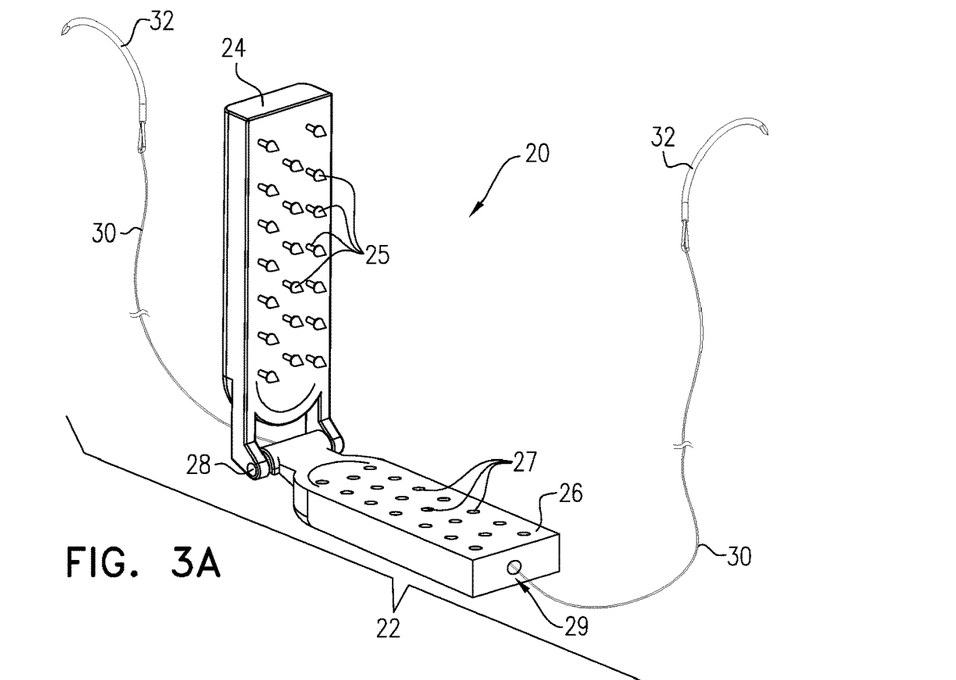
FIGS. 3A-B are schematic illustrations of the extraocular muscle clip coupled to a suture, in accordance with some applications of the present invention.
Figure 3B:
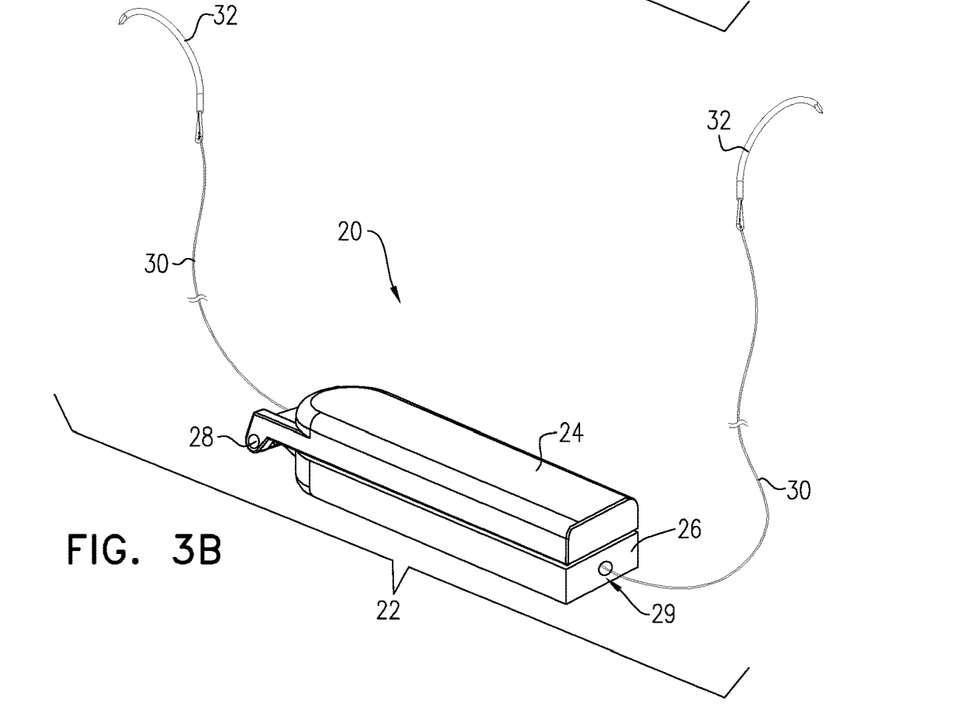

Reference is still made to FIG. 1, and is additionally made to FIG. 3A-B, which are schematic illustrations of extraocular muscle clip 22 coupled to a suture 30, in accordance with an application of the present invention. Typically, upper and lower plates 24 and 26 comprise corresponding planar surfaces which provide increased surface area in order to sandwich extraocular muscle 42 therebetween. Upper and lower plates 24 and 26 are shaped so as to define respective rectangles by way of illustration and not limitation. It is to be noted that the upper and lower coupling elements may be provided in any suitable shape. As shown, upper plate 24 is shaped so as to define a plurality of male coupling elements 25. Each coupling element 25 comprises a pointed distal tip so as to puncture through tissue of muscle 42, a post coupled to the pointed distal tip and a barb close to the tip so as to facilitate irreversible coupling between upper and lower plates 24 and 26. Lower plate 26 is shaped so as to define a plurality of corresponding female coupling elements 27, e.g., openings, which are each shaped so as to receive a respective male coupling element 25. It is to be noted upper plate 24 may be shaped to define female coupling elements 27 while lower plate 26 may comprise male coupling elements 25 (configuration not shown). Once plate 24 is moved toward plate 26, male coupling elements 25 puncture tissue of muscle 42, and then fit within female coupling elements 27 and are locked in place due to the barbs.

For some applications, upper and lower plates 24 and 26 are coupled together by a hinge 28. It is to be noted that clip 22 may comprise upper and lower plates 24 and 26 independently of hinge 28. In such applications of the present invention, upper and lower plates 24 and 26 comprise discrete elements which are held in separate from each other when in the delivery state of clip 22 by different elements of delivery tool 50, and are moveably together by the respective components of tool 50. For some applications of the present invention, clip 22 does not comprise hinge 28, rather, delivery tool 50 comprises hinge 28 (e.g., hinge 28 may be coupled to muscle hook 56) which is used to couple together upper and lower plates 24 and 26. Once upper and lower plates 24 and 26 are coupled together, hinge 28 is removed from clip 22 by retracting and/or moving tool 50.

Typically, suture 30 is coupled to either upper or lower plates 24 and 26. As shown by way of illustration and not limitation, suture 30 is coupled to lower plate 26. It is to be noted that suture 30 may be coupled to upper plate 24. As shown, suture 30 is slidable through a lumen 29 defined by lower plate 26 (as shown in FIG. 3B). For some applications of the present invention, suture 30 is fixedly coupled to plate 26. Suture 30 typically comprises suture needles 32 at respective ends thereof. For some applications, suture 30 comprises a fabric. For some applications of the present invention, suture 30 is replaced by a wire.

For some applications, extraocular muscle clip 22 and/or suture 30 comprise a dissolvable material.

Reference is again made to FIG. 1. For some applications, lower plate 26 is disposed within a housing or a recessed portion provided by muscle hook 56, as shown. For some applications of the present invention, muscle hook 56 is coupled to or comprises a mount to which lower plate 26 is coupled. During delivery of clip 22 to muscle 42, plate 24 is held distanced from plate 26 in the delivery state. Muscle hook 56 is slid underneath muscle 42 so as to position lower plate 26 underneath muscle 42 and in between the sclera and the under surface of muscle 42. During delivery, suture 30 is positioned with respect to tool 50 in a manner in which suture needles 32 coupled to suture 30 are disposed safely and are not exposed as they appear in FIG. 1. For example, suture needles 32 may be disposed within a lumen of shaft 52.

Muscle hook 56 may be moved underneath any of the extraocular muscles, e.g., the superior rectus, the inferior rectus, the medial rectus, the lateral rectus, the superior oblique muscle, or the inferior oblique muscle. FIG. 1 shows a state of system 20 in which muscle hook 56 has been positioned underneath muscle 42 of an eye 40 of a patient that has strabismus.

Figure 4A:
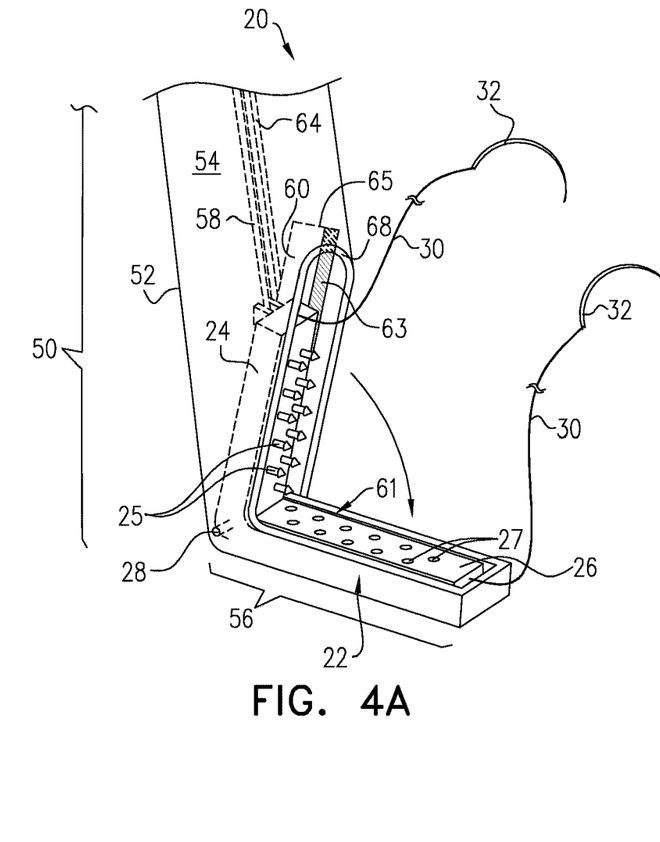
FIGS. 4A-B are schematic illustrations of the operation of the mechanism of the integrated blade of the delivery tool, in accordance with some applications of the present invention.
Figure 4B:
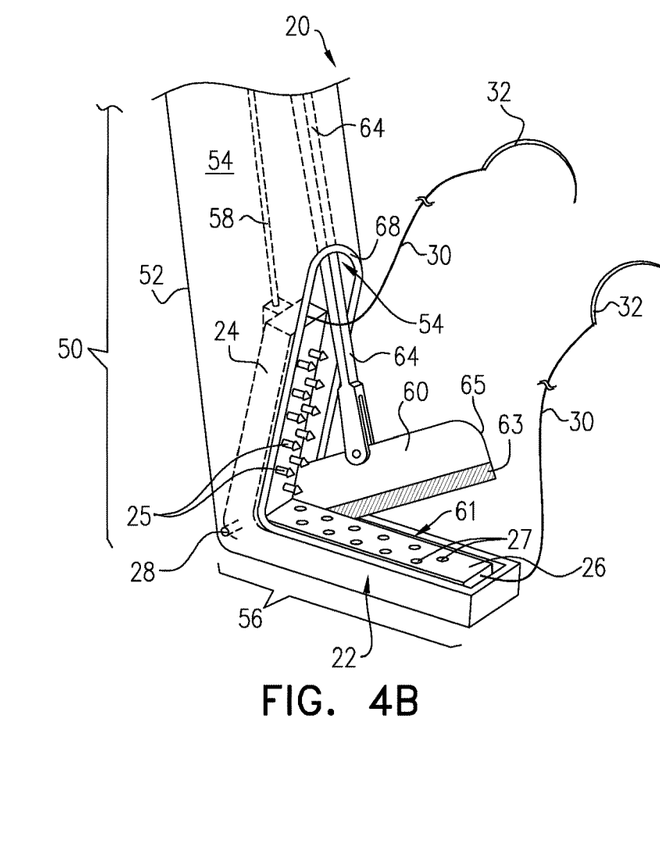

Reference is still made to FIG. 1, and is additionally made to FIGS. 4A-B, which are schematic illustrations of the operation of the mechanism of integrated blade 60 of delivery tool 50, in accordance with an application of the present invention. When tool 50 is in the state in which hook 56 delivers lower plate 26 underneath muscle 42 and upper plate 24 is moved toward lower plate 26 and subsequently coupled thereto, blade 60 is generally in alignment with a longitudinal axis of shaft 52 of delivery tool 50. For some applications, when tool 50 is in the state in which hook 56 delivers lower plate 26 underneath muscle 42 and upper plate 24 is moved toward lower plate 26 and subsequently coupled thereto, blade 60 is disposed generally in parallel with upper plate 24. In either application, during movement of hook 56 and lower plate 26 underneath muscle 42, blade 60 is kept in a position in which it is maintained in a safe position to prevent premature and inadvertent cutting of tissue during delivery of lower plate 26. Shaft 52 is shaped so as to define a slit or opening at a distal end of shaft 52. During delivery of lower plate 26, blade 60 is maintained within the slit, as shown in FIG. 4A. For some applications, blade 60 is disposed with respect to the slit in a manner in which a terminal, distal end 65 of blade 60 is disposed within a lumen 54 of shaft 52 in a location that is proximal to a proximal end 68 of the slit. That is, for some applications, during delivery of lower plate 26, blade 60 is maintained at least in part within lumen 54 of shaft 52. Once plate 26 is positioned, blade 60 is slidable with respect to shaft 52 distally so as to expose distal end 65 from within the slit in order to facilitate movement of a cutting edge 63 of blade 60 toward muscle 42, as is described hereinbelow.

For some applications of the present invention, blade 60 is disposed entirely and slidable within lumen 54 of shaft 52 during delivery of clip 22 to muscle 42.

Figure 2:
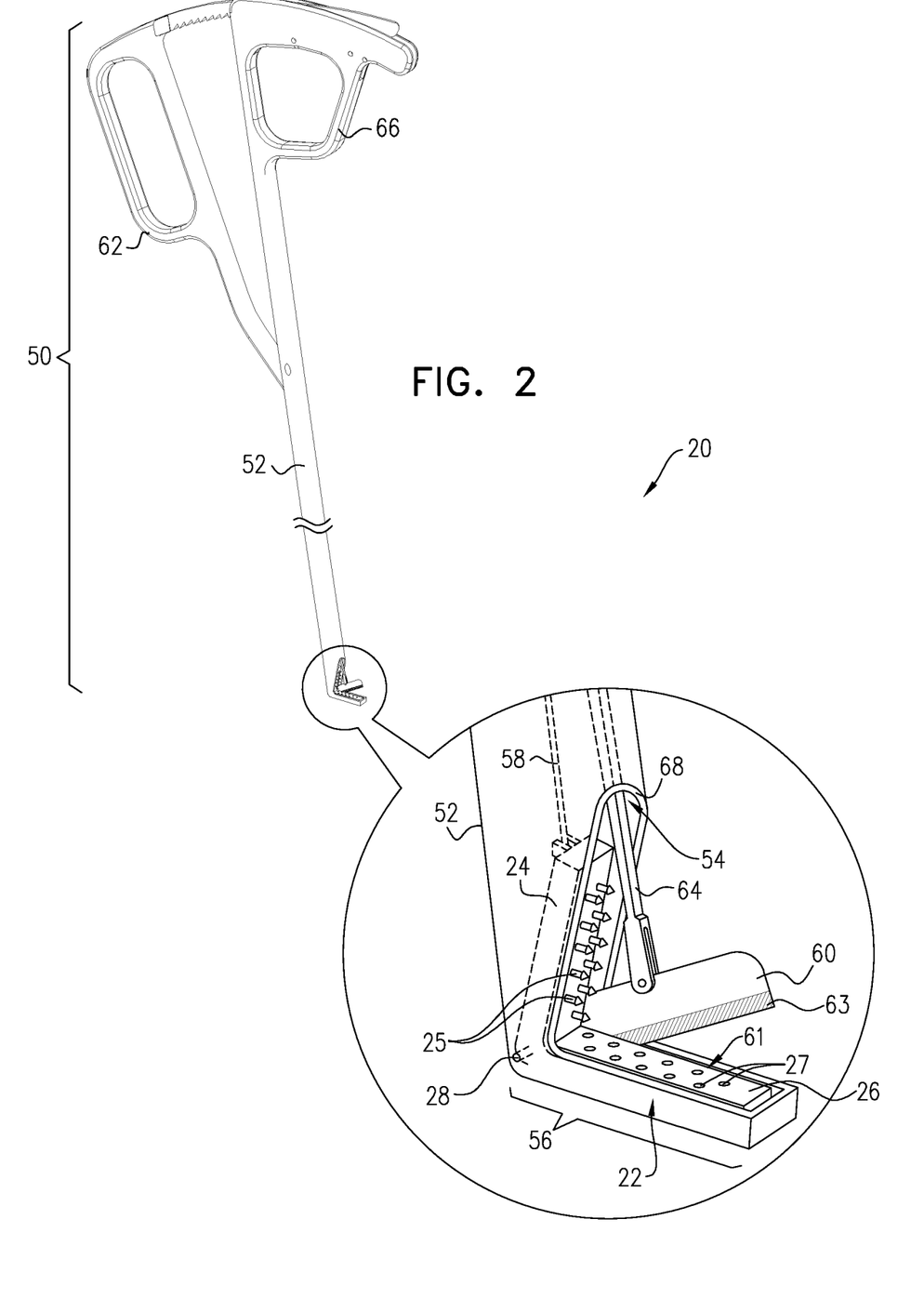
FIG. 2 is a schematic illustration of the delivery tool and its components, in accordance with some applications of the present invention.

Reference is still made to FIGS. 4A-B, and is additionally made to FIG. 2, which is a schematic illustration of delivery tool 50 and its components, in accordance with an application of the present invention. Blade 60 is coupled to a distal end of an elongate control shaft 64 which facilitates movement of blade 60. A proximal end of control shaft 64 is coupled to a handle portion at the proximal end of delivery tool 50. For some applications, as shown in FIG. 2, the handle portion comprises a stationary finger ring 66 and a moveable finger ring 62. Movement of ring 62 toward ring 66 facilitates distal movement of control shaft 64 so that blade 60 is moved angularly downward, as shown in FIG. 4B. It is to be noted that tool 50 comprises ring 62 by way of illustration and not limitation. It is to be noted that a trigger may be used instead of ring 62. For applications in which at least a part of blade 60 is disposed within lumen 54 of shaft 52 during delivery of clip 22, control shaft 64 facilitates longitudinal distal sliding of blade 60 with respect to shaft 52 prior to facilitating angular downward movement of blade 60.

Once lower plate 26 of clip 22 is positioned underneath muscle 42, and clip 22 is closed to capture muscle 42, as is described hereinbelow, the operating physician moves ring 62 toward ring 66 in order to facilitate movement of integrated blade 60.

Reference is now made to FIGS. 1, 2, and 4B. FIGS. 1, 2, and 4B illustrate movement of the blade 60 with respect to shaft 52. The several states shown do not actually occur during use of the delivery tool 50 during an operating procedure. That is, during the operating procedure, blade 60 is moved only once clip 22 is in the grasping state in which upper plate 24 is coupled to lower plate 26 so as to sandwich muscle 42 between plates 24 and 26 in order to facilitate grasping of muscle 42 by clip 22, as shown hereinbelow with reference to FIG. 7. The step-wise procedure of the use of delivery tool 50 and clip 22 is shown in FIGS. 5-9, described hereinbelow.

As shown in FIGS. 2 and 4A-B, for some applications, muscle hook 56 is shaped so as to define a groove 61 for receiving cutting edge 63 of blade 60 once blade 60 cuts muscle 42. For some applications, groove 61 is disposed between lower plate 26 and an edge of hook 56. Groove 61 prevents movement of blade 60 beyond muscle hook 56 so as to prevent continued cutting of tissue by blade 60, and thereby groove 61 functions as a safety to prevent inadvertent cutting of the sclera. For some applications, hook 56 does not define a groove, but instead defines a spatial planar surface that is disposed in the angular path of blade 60 such that hook 56 prevents movement of blade 60 beyond muscle hook 56 so as to prevent continued cutting of tissue by blade 60, and thereby hook 56 functions as a safety to prevent inadvertent cutting of the sclera.

Figure 5:
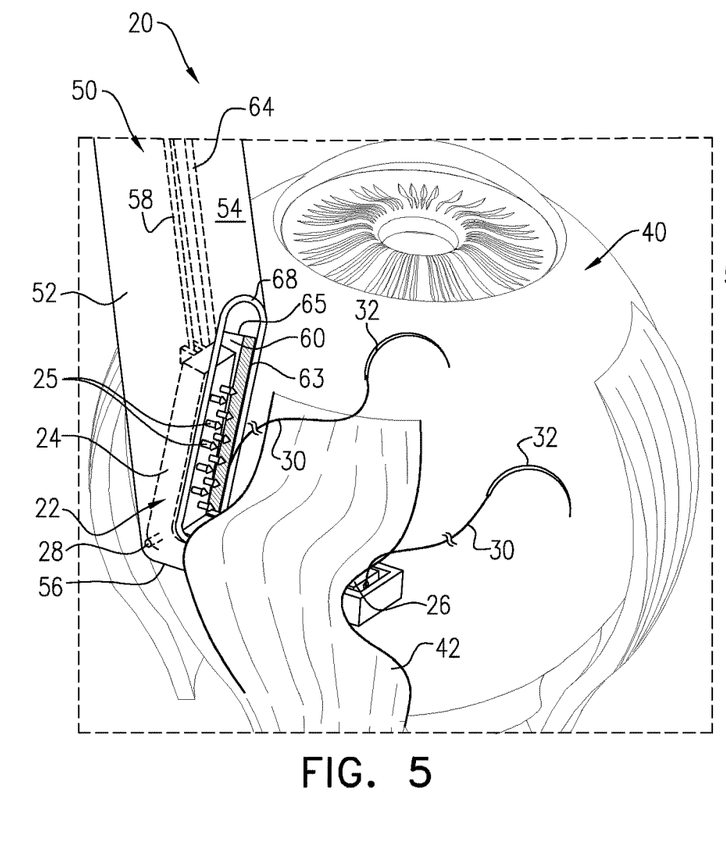
FIGS. 5-9 are schematic illustrations of the steps of the strabismus surgery procedure using the delivery tool and clip described in FIGS. 1-4B, in accordance with some applications of the present invention.

Reference is now made to FIGS. 5-9, which are schematic illustrations of the steps of a method using system 20 comprising delivery tool 50 and extraocular muscle clip 22 to correct strabismus of the patient, in accordance with some applications of the present invention. As shown in FIG. 5, muscle hook 56 is positioned underneath extraocular muscle 42 in order to position lower plate 26 of extraocular muscle clip 22 underneath muscle 42. As described hereinabove, suture needles 32 are shown exposed by way of illustration and not limitation, and needles 32 may be disposed within lumen 54 of tool 50 during delivery. As shown, during delivery of hook 56 underneath muscle 42, and during the closing of upper plate 24 toward lower plate 26, blade 60 is maintained in a position in which blade 60 is in general alignment with shaft 52 and disposed generally in parallel with upper plate 24. As shown, distal end 65 of blade 60 is exposed from within lumen 54 by way of illustration and not limitation. It is to be noted that distal end 65 of blade 60 may be disposed within lumen 54 of shaft 52, as described hereinabove with reference to FIG. 4A.

As shown in FIG. 6, once lower plate 26 is positioned underneath muscle 42, upper plate 24 is moved toward muscle 42. That is, delivery tool 50 facilitates delivery of upper plate 24 above extraocular muscle 42 such that upper plate 24 is movable toward an upper surface of extraocular muscle 42 and couplable together with lower plate 26 to sandwich and grasp extraocular muscle 42. For some applications of the present invention, as shown, upper plate 24 is reversibly coupled to a control shaft 58 via a connector 59 at the upper surface of upper plate 24. Control shaft 58 is moveable by the operating physician in order to facilitate closing of upper plate 24 with lower plate 26. As shown, shaft 58 facilitates downward angular movement of plate 24 toward muscle 42 and toward plate 26 disposed underneath muscle 42. Force is applied to plate 24 so as to facilitate puncturing of muscle tissue by male coupling elements 25 of upper plate 24. In such a manner, muscle 42 is sandwiched between upper and lower plates 24 and 26. Further force is applied to plate 24 so that male coupling elements 25 of upper plate 24 mate with female coupling elements 27 of lower plate 26 in a manner in which upper and lower plates 24 and 26 are secured together in order to facilitate grasping of muscle 42 by clip 22. For some applications of the present invention, male coupling elements 25 are shaped so as to define a barb which facilitates irreversible coupling between elements 25 and 27.

It is to be noted that delivery tool 50 comprises control shaft 58 by way of illustration and not limitation. For some applications, the operating physician may use his/her fingers to move plate 24 toward plate 26.

During the transition of upper and lower plates 24 and 26 from the delivery state of clip 22 to the grasping state of clip 22, blade 60 remains in a position in which it is in general alignment with shaft 52 of tool 50, as shown in FIG. 60.

As shown in FIG. 7, once muscle 42 is grasped by clip 22, the operating physician facilitates movement of blade 60 toward the upper surface of muscle 42. That is, the physician moves moveable finger ring 62 shown in FIG. 2 toward stationary finger ring 66 so as to facilitate distal sliding of blade 60 with respect to shaft 52 and/or angular movement of blade 60 downward with respect to muscle 42. Movement of ring 62 facilitates movement of shaft 64 so as to push blade 60 angularly distally. Cutting edge 63 of blade 60 is brought into contact with muscle 42 in order to sever muscle 42. Once muscle 42 is initially severed and disinserted, any suitable strabismus surgery may be performed, e.g., resection or recession.

As described hereinabove, muscle hook 56 and/or groove 61 of hook 56 stop continued movement of blade 60 beyond muscle hook 56 so as to prevent inadvertent cutting of the sclera by blade 60.

Figure 8:
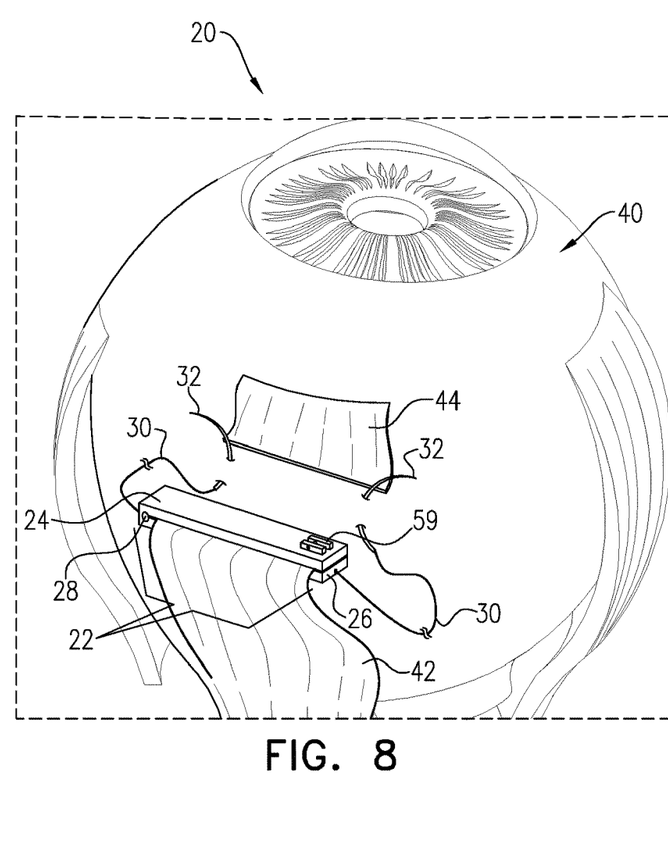

As shown in FIG. 8, tool 50 is decoupled from clip 22, and muscle 42, which is grasped by clip 22, is then recoupled to eye 40 (e.g., to a globe of the eye). Recoupling of muscle 42 to eye 40 can be performed using the hang-back procedure, the non-hang-back procedure, procedures in which the disinserted muscle coupled to clip 22 is sutured (a) to the sclera in a vicinity of stump 44 (e.g., underneath stump 44) from the original insertion (as shown), (b) directly to a stump 44 from the original insertion and to the sclera (not shown), (c) to the sclera in any suitable vicinity of the eye (not shown), and/or to any suitable tissue as decided by the operating physician FIG. 8 shows the hang-back procedure in which suture 30 is sutured underneath stump 44 using needles 32 so as to draw the disinserted muscle 42, grasped by clip 22, toward eye 40.

Figure 9:
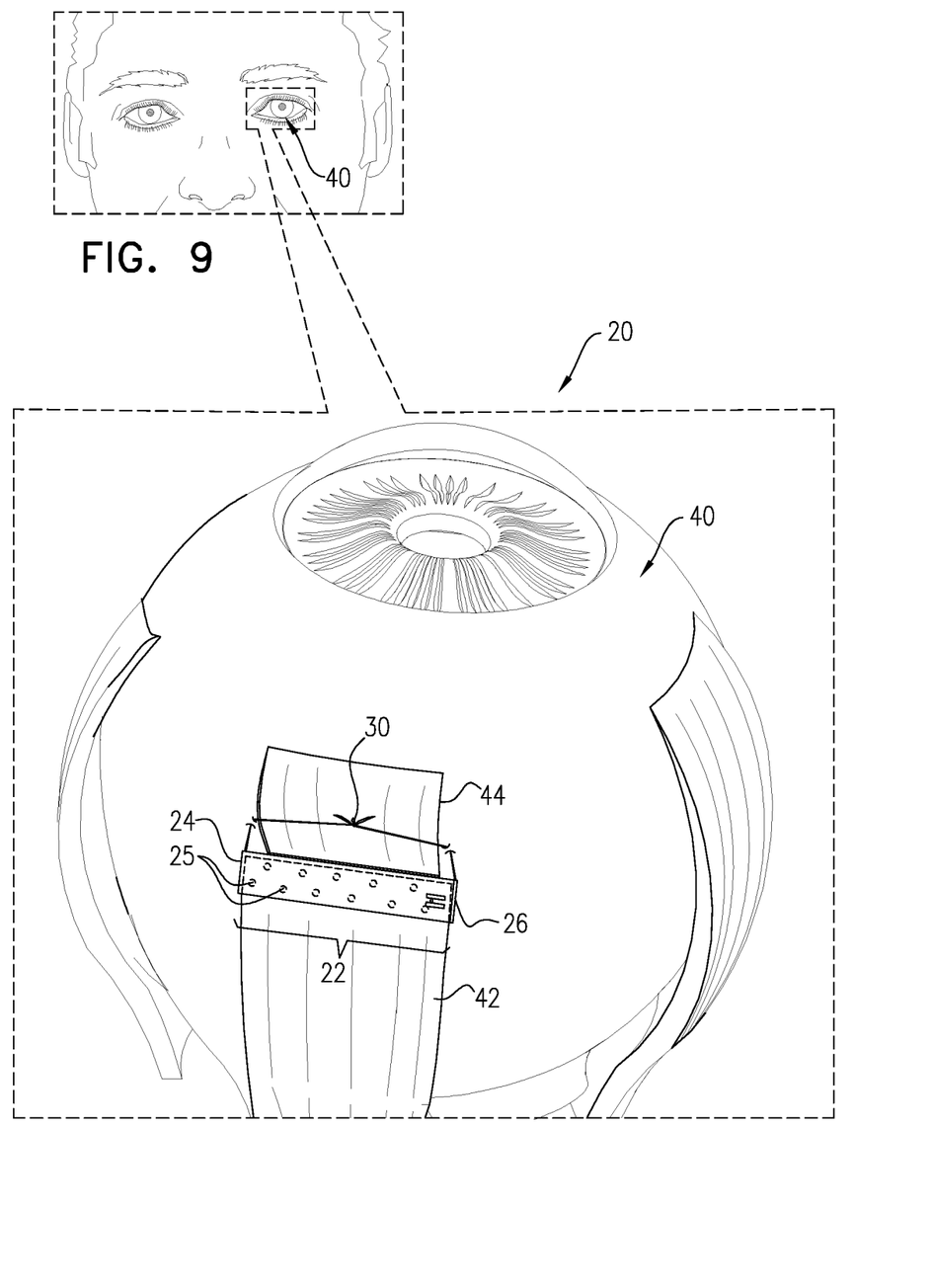

As shown in FIG. 9, the strabismus of the patient is corrected, and clip 22 remains coupled to muscle 42. For some applications clip 22 and/or suture 30 is dissolvable, or absorbable.

Reference is now made to FIGS. 1-9. It is to be noted that system 20 including tool 50 and clip 22 may be used to fix strabismus using any suitable procedure, e.g., recession, resection, and/or any other suitable procedure. It is to be noted that system 20 including tool 50 and clip 22 may be used to perform strabismus surgery using a hang-back procedure and/or a non-hang-back procedure. It is to be noted that system 20 including tool 50 and clip 22 may be used may be used to perform any other ocular surgical procedure that involves manipulation of the extraocular muscle.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for correcting strabismus of an eye of a patient, the method comprising:
    delivering an extraocular muscle clip including an upper plate and a lower plate to an extraocular muscle using an elongate delivery tool including:
        an elongate shaft reversibly coupled to the extraocular muscle clip,
        a muscle hook at a distal end of the elongate shaft, the muscle clip being reversibly coupled to the elongate shaft in a manner in which the lower plate of the muscle clip is coupled to the muscle hook and is distanced from the upper plate during the delivering;
    positioning the lower plate underneath the extraocular muscle by sliding the muscle hook underneath the extraocular muscle;
    subsequently to the positioning:
        moving the upper plate of the muscle clip to an upper surface of the extraocular muscle;
        sandwiching the extraocular muscle between the upper and lower plates; and
        grasping the extraocular muscle between the upper and lower plates by coupling together the upper and lower plates;
    subsequently to the grasping:
        distally moving an integrated blade of the delivery tool with respect to the elongate shaft of the elongate delivery tool; and
        cutting the extraocular muscle with the integrated blade; and
    subsequently to the cutting, recoupling the extraocular muscle to the eye by suturing to the eye one or more sutures coupled to at least one of the upper plate or the lower plate of the muscle clip and by the suturing, drawing the muscle clip and the extraocular muscle grasped by the muscle clip toward the eye.

2. The method according to claim 1, wherein the elongate shaft includes a tube, and wherein the method further includes sliding the integrated blade at least in part within a lumen of the tube of the delivery tool and exposing the blade from within the lumen of the tube so that the blade can cut the extraocular muscle.

3. The method according to claim 1, wherein the muscle clip includes a hinge coupling the upper plate and lower plate.

4. The method according to claim 1, wherein the muscle hook is coupled to the elongate shaft, and wherein the muscle hook prevents movement of the blade beyond the muscle hook.

5. The method according to claim 1, wherein the extraocular muscle clip is dissolvable.

6. The method according to claim 1, wherein the delivery tool includes an arm reversibly coupled to the upper plate, and wherein the method comprises moving the arm to move the upper plate in order to couple together the upper plate and the lower plate such that the upper and lower plates assume a grasping state.

7. The method according to claim 1, wherein the one or more sutures are threaded through at least one of the upper plate or the lower plate of the muscle clip.

* * * * *